United States Patent [19]

Schachter et al.

[11] Patent Number: 4,537,718

[45] Date of Patent: Aug. 27, 1985

[54] IMPERMEANT SPECTROSCOPIC PROBES

[75] Inventors: David Schachter, Bronx, N.Y.; Richard E. Abbott, Englewood, N.J.; Uri Cogan, Haifa, Israel

[73] Assignee: Columbia University in the City of New York, New York, N.Y.

[21] Appl. No.: 436,799

[22] Filed: Oct. 26, 1982

[51] Int. Cl.$^3$ .................. C07C 103/52; G01N 21/84
[52] U.S. Cl. .................. 260/112.5 R; 436/60; 436/63; 436/518
[58] Field of Search .................. 260/112.5 R; 436/63, 436/60, 518

[56] References Cited

U.S. PATENT DOCUMENTS

| | | | |
|---|---|---|---|
| 3,645,696 | 2/1972 | Iannacone et al. | 436/60 |
| 3,891,670 | 6/1975 | Kanaoka et al. | 548/549 |
| 3,940,475 | 2/1976 | Gross | 436/518 |
| 3,992,631 | 11/1976 | Horte | 436/63 |
| 4,018,884 | 4/1977 | Cleeland, Jr. et al. | 260/112.5 L |
| 4,225,485 | 9/1980 | Buckler et al. | 260/112.5 L |
| 4,238,395 | 12/1980 | Buckler et al. | 260/112.5 L |
| 4,259,233 | 3/1981 | Corrico et al. | 260/112.5 L |
| 4,261,893 | 4/1981 | Boguslaski et al. | 260/112.5 L |
| 4,315,853 | 2/1982 | Fujino et al. | 260/112.5 R |
| 4,318,846 | 3/1982 | Khanna et al. | 260/112.5 L |
| 4,326,008 | 4/1982 | Rembaum | 260/112.5 L |
| 4,331,760 | 5/1982 | Berger et al. | 436/63 |
| 4,334,069 | 6/1982 | Buckler et al. | 260/112.5 L |
| 4,345,027 | 8/1982 | Dolbeare | 436/63 |
| 4,351,760 | 9/1982 | Khanna et al. | 260/112.5 L |
| 4,358,535 | 11/1982 | Falkow et al. | 436/63 |
| 4,388,233 | 6/1983 | Bissell et al. | 260/112.5 L |
| 4,388,412 | 6/1983 | Yabusaki | 436/63 |
| 4,409,140 | 10/1983 | Smith et al. | 260/112.5 L |

OTHER PUBLICATIONS

Abbot et al, *Journal of Biological Chemistry*, 251, 7176–7183, (1976).

*Primary Examiner*—Delbert R. Phillips
*Attorney, Agent, or Firm*—Oblon, Fisher, Spivak, McClelland & Maier

[57] ABSTRACT

Lipid-soluble impermeant spectroscopic probes for the study of intact biological membranes are disclosed.

6 Claims, 8 Drawing Figures

SCHEMATIC REPRESENTATION OF MEMBRANE-IMPERMEANT
SPECTROSCOPIC PROBES, WHERE
MIM = MEMBRANE IMPERIMENT MOIETY
A = ARM
R = SPECTROSCOPIC REPORT GROUP

STRUCTURAL REPRESENTATION OF N-OLIGOSACCHARIDE ALKYL
DICARBOXYLIC ACID DIHYDRAZIDE INTERMEDIATE WHEREIN THE
OLIGOSACCHARIDE IS STACHYOSE AND n=2.

N-STACHYOSE-SUCCINIC ACID DIHYDRAZIDE (COMPOUND I)

A. Oligosaccharide Derivatives

B. Glutathione Derivatives

IMPERMEANT SPECTROSCOPIC PROBES

BACKGROUND OF THE INVENTION

Support of National Institute of Health Grants HL16851 and AM21238 in the performance of the work described herein is acknowledged.

FIELD OF THE INVENTION

The present invention relates generally to fluorophores and to other spectroscopic probes, more particularly to impermeant spectroscopic probes especially useful for quantification of lipid fluidity in plasma membranes.

DESCRIPTION OF THE PRIOR ART

It is well-established that plasma membranes are bilayers of lipids which contain proteins or lipo-protein complexes. It is further known that the lipids in the plasma membranes occur in hemileaflets which differ in lipid composition. Considerable evidence also indicates that the molecular organization of biological membranes is anisotropic.

Given the anisotropy and widespread occurrence of lipid asymmetry in the leaflets of biological membranes, a number of investigators have sought to determine the importance and function of the structural and organizational differences in the membrane lipids. The issue is of considerable importance because the physicochemical state of the lipids is a significant determinant and modulator of such important membrane functions as adsorption, permeability, transport, membrane biogenesis, enzymatic and metabolic processes, and hormonal regulation.

Experimental evidence suggests that the molecular organization of the membrane lipids and proteins controls such vectorial cellular functions as selective ion exchange, solute transfer, selective surface adsorption and the like. Much of the evidence derives from the application of membrane-impermeant probes, i.e., reagents confined to one surface. A number of impermeant probes including enzymes, antibodies, lectins, enzyme substrates, inhibitors, small molecular weight functional group reagents and the like have been employed in such studies. The application of lipid-soluble fluorophores and other spectroscopic probes for assessment of membrane functions has also been known.

It should be noted, however, that the data obtained from the study of lipid-soluble or permeant fluorophores and other spectroscopic probes are difficult to interpret because the fluorescence or other signal emitted is a mixed signal from both the outer and the inner leaflets of the membrane as well as from intracellular membrane organelles. Being lipid soluble and permeant, the probes distribute in both leaflets of the membrane and, therefore, do not distinguish between the outer and inner hemileaflets of the bilayer. Furthermore, being lipid soluble and permeant, the probe molecules exhibit transverse diffusion across the membrane, i.e., they flip from one membrane leaflet to the other and permeate to the cytosol and internal organelles of intact cells. Hence, the study of the lipid fluidity of cells or parts thereof with permeant lipid fluorophores yields data which are difficult of precise interpretation.

The spectroscopic probes of the present invention are novel and distinguishable from other impermeant probes heretofore known in at least the following unique characteristics:

(1) The probes of the present invention interact noncovalently with the membrane, whereas prior art compounds cause covalent modification of the membrane;

(2) The probes of the present invention provide dynamic information by virtue of their spectral properties, whereas the prior art compounds provide static information by virtue of their reactive properties;

(3) The probes of the present invention have spectroscopic reporter groups which partition into membrane lipids whereas the prior art probes react with membrane proteins and do not have reporter groups.

SUMMARY OF THE INVENTION

It is, therefore, an object of the present invention to provide impermeant spectroscopic probes including electron spin resonance (ESR) probes suitable for the study of membranes.

It is another object of the present invention to provide a family of lipid-soluble impermeant spectroscopic probes suitable for the study of intact biological membranes.

It is yet another object of the present invention to provide impermeant lipid-soluble probes with spectral properties suitable for assessment of lipid fluidity of the outer hemileaflet of the plasma membranes of intact cells.

A further object of the present invention is to provide an impermeant spectroscopic probe wherein impermeant substituents prevent transverse diffusion of the probe from one hemileaflet to the other.

A still further object of the present invention is to provide spectroscopic probes having sufficient nonpolar characteristic to bring about efficient partition into the lipids of the membrane.

A yet another object of the present invention is to provide a fluorophore having distinctly separable excitation and emission peaks close to or in the visible spectrum for convenience in fluorescence microscopy.

A further object of the present invention is to provide a fluorophore having fluorescence lifetimes sufficient for good signals but short enough to provide readily-quantified fluorescence anisotropy values.

An additional object of the present invention is to provide a probe having a membrane-impermeant moiety linked to pyrene via a connecting arm.

A further object of the present invention is to provide spectroscopic probes of water-soluble membrane-impermeant conjugates of a saccharide and 7-nitrobenz-2-oxa-1,3diazole (NBD) having a connecting arm between the saccharide and NBD (or coumarin derivatives, acridine derivatives, bimane derivatives, stilbene derivatives, anthracene derivatives, parinaric acid (cis and trans), anthranilates and the like) or other spectroscopic probe.

Another object of the present invention is to provide an alkyl hydrazide linked to a saccharide as a useful intermediate for the synthetic coupling under mild conditions of spectroscopic reporter groups to a saccharide.

A still another object of the present invention is to provide classes of oriented reagents and methods of preparing the same wherein their structures can be varied systematically for the study of structure-activity relationships.

Another object of the present invention is to provide probes suitable for the study of rotational and short or long range lateral diffusion in conjunction with methods for the estimation of fluorescence polarization, fluorescence excimer intensity, fluorescence photobleach recovery and the like.

A further object is to provide probes suitable for the study of surface properties of normal and abnormal cells as an aid in the diagnosis of cellular and surgical pathology.

Other objects and advantages will become apparent as the description proceeds.

The attainment of these and other objects is made possible by this invention which includes an impermeant spectroscopic probe comprising a membrane impermeant moiety joined by suitable linkage group to a spectroscopic reporter group and a method of preparing the same.

BRIEF DESCRIPTION OF THE DRAWINGS

A more complete appreciation of the invention and many of the attendant advantages thereof will be readily perceived, as the same becomes better understood by reference to the following detailed description when considered in connection with the accompanying figures, wherein.

DETAILED DESCRIPTION OF THE INVENTION

In order to achieve hereinabove enumerated and other objects and advantages of the present invention, the spectroscopic probe should have certain characteristics including:

(a) impermeant substituents to prevent transverse diffusion from one hemileaflet to the other;

(b) sufficient nonpolar character to bring about efficient partition into the lipid of the membrane; and (c) for fluorescence microscopy fluorophores should have excitation and emission peaks in the visible spectrum with good separation of the peaks and a reasonably short lifetime.

Figure 1:
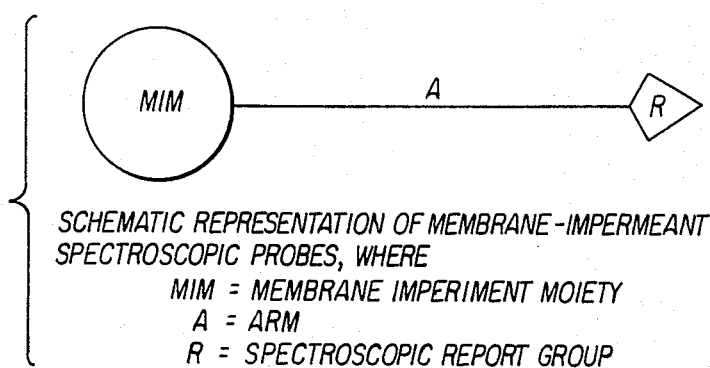
FIG. 1 is a schematic representation of membrane impermeant spectroscopic probes.

FIG. 1 shows a basic design according to the present invention of fluorophore probes having the characteristics mentioned above. The probe comprises (1) a membrane-impermeant moiety; (2) an arm; and (3) a spectroscopic reporter group.

In these probes the membrane impermeant moiety may be, for example, a saccharide, such as an oligosaccharide or a peptide, such as a tripeptide. The arm may be a membrane-permeable entity generally of a hydrocarbon nature; and the spectroscopic reporters may be either fluorescent or stable free radical groups. The synthesis of these novel probes is based on the development of a new family of versatile intermediates which incorporate both the membrane impermeant oligosaccharide and an arm which allows the attachment of a variety of spectroscopic reporter groups under mild conditions.

Figure 2:
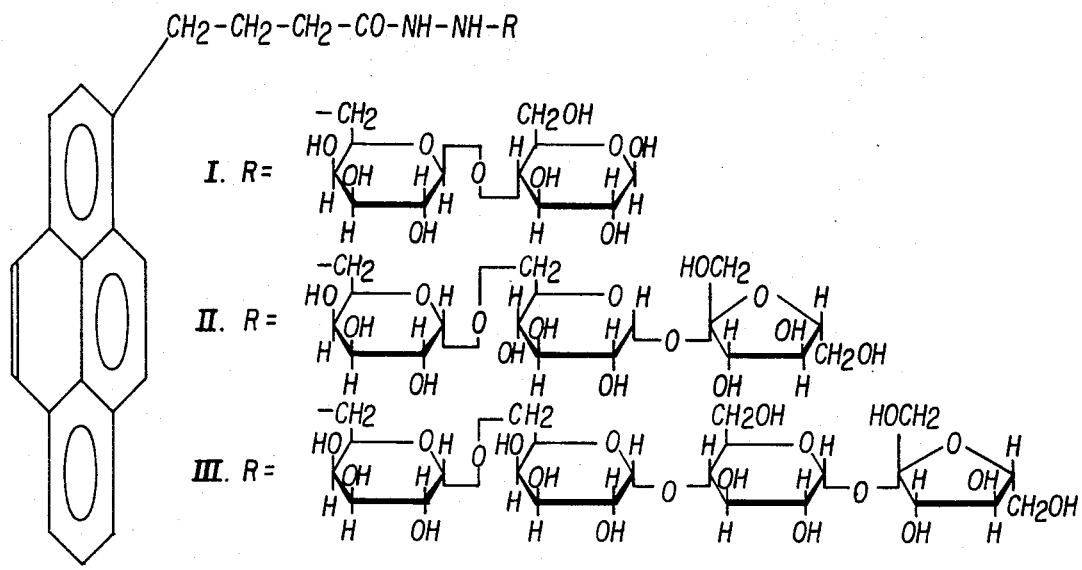
FIG. 2 is a structural representation of some impermeant pyrene-linked derivatives.
Figure 2:
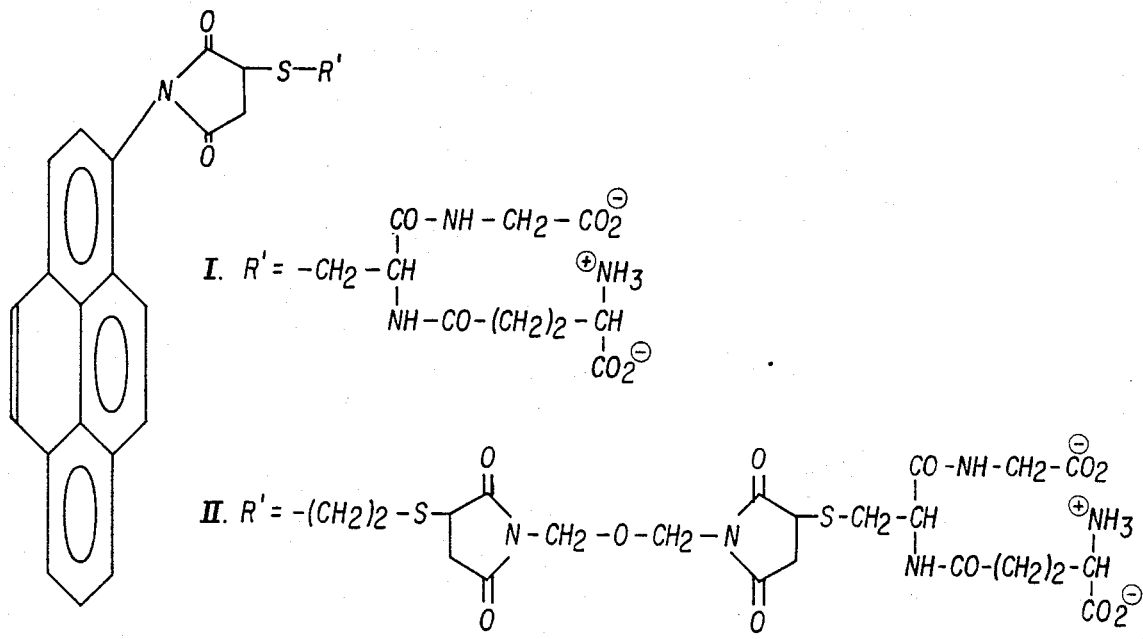

FIG. 2 shows structures of certain impermeant pyrene-linked derivatives. The oligosaccharide derivatives (A) have membrane-impermeant substituents derived, respectively, from lactose (I), raffinose (II) and stachyose (III). The glutathione derivatives (B) differ from each other in the length and nature of the connecting arms.

Figure 3:
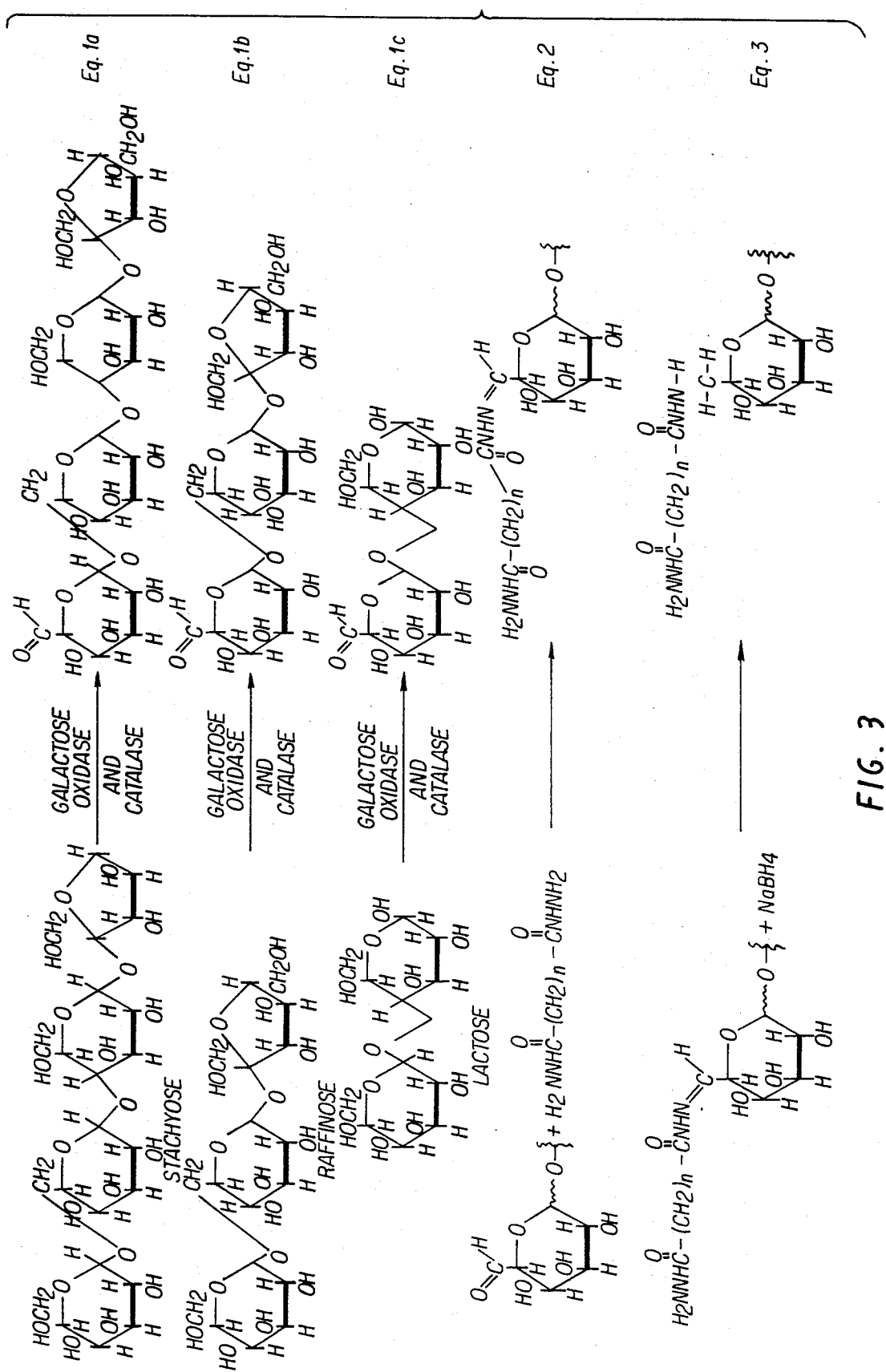
FIG. 3 is a representation of the reaction schemes for the preparation of oligosaccharide alkyldicarboxylic acid dihydrazides.

FIG. 3 shows reaction schemes for the preparation of oligosaccharide alkyldicarboxylic acid dihydrazides using various membrane impermeant moieties.

Figure 4:
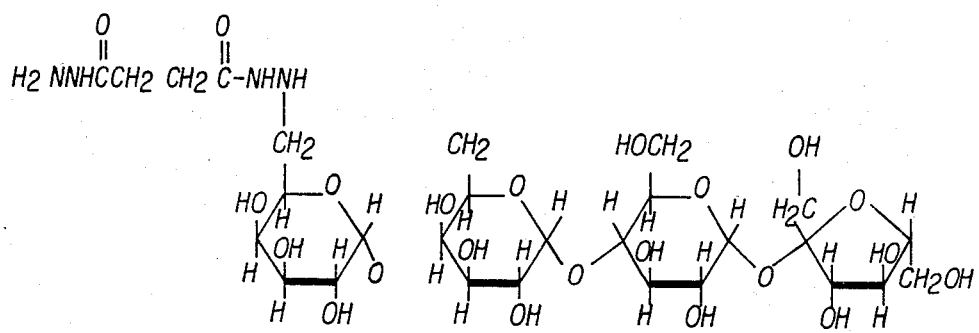
FIG. 4 is a structural representation of an N-oligosaccharide alkyl dicarboxylic acid dihydrazide intermediate wherein the oligosaccharide is stachyose and n=2.

FIG. 4 shows the structure of an N-oligosaccharide alkyldicarboxylic acid dihydrazide intermediate wherein the oligosaccharide is stachyose and n=2.

Any saccharide which will form an impermeant spectroscopic probe having the characteristics described supra can be used. Saccharides which have been found to be preferable are oligosaccharides, e.g., lactose, raffinose, stachyose and the like. Of course, other saccharides well-known to those skilled in the art could equally well be utilized in the practice of this invention.

As to peptides, any peptide which will form an impermeant fluorophore having the characteristics described supra can be used. Peptides which have been found to be preferable are glutathione and other monocysteinyl peptides. Of course, other peptides well-known to those skilled in the art could also be utilized in the practice of this invention.

In order to prepare the spectroscopic probes including ESR probes and fluorophores according to the present invention, the saccharide, if it has a terminal alcohol group, should be treated with a suitable agent, preferably an enzyme, e.g., an oxidase, to oxidize the terminal alcohol group to an aldehyde. According to one embodiment of the present invention, the product is then reacted with a suitable hydrazide to form a Schiff's base which is then reduced with borohydride to yield a saccharide-substituted hydrazide. The resulting compound is then used in a variety of syntheses. For example, it may be treated with NBD-Cl to yield an impermeant NBD (7-nitrobenzo-2-oxa-1,3-diazole) fluorophore.

Among pyrenes which could be advantageously used in the preparation of the probes of the present invention, pyrenebutyryl hydrazide, N-(1-pyrenyl) maleimide, N-(1-pyrenyl)iodoacetamide, pyrenebutyric acid, pyrene decanoic acid, pyrenehexadecanoic acid and pyrene isothiocyanate are preferable. Of course, other pyrenes or derivatives thereof suggested to those skilled in the art could also be employed in the practice of this invention.

Among NBD, the preferable compounds are NBD-Cl, N-(NBD-4-yl)aziridine, 6-(NBD-4-yl)aminohexanoic acid, 12-(N-methyl-N-NBD-4-yl)aminododecanoic acid and the like.

The dihydrazides which can be used in the synthesis of the fluorophores are adipic dihydrazide (n=4) and other dihydrazides (n=6, 8, 10, ...). A consideration in the selection of the dihydrazide is that the final product should have a proper hydrophobic/hydrophilic balance.

Among anthracenes some preferable compounds are anthracene-9-carboxaldehyde and anthroyloxy derivatives of fatty acids such as 2-(9-anthroyloxy)stearic acid, 16-(9-anthroyloxy)palmitelaidic acid, 12-(9-anthroyloxy)stearic acid and the like.

Coumarin derivatives, bimane derivatives, stilbene derivatives, anthracene derivatives, parinaric acid (cis and trans), anthranilates and the like are also useful.

Among the ESR probes which can be used are 5-doxylstearic acid, 12-doxylstearic acid, 2,2,5,5-tetramethyl-3-pyrolidin-1-oxyl-3carboxylic acid and the like.

The fluorophores and stable free radical groups that are listed above are readily available commercially; they and others may also be synthesized by standard methods well known in the art.

Some of the spectroscopic probes including ESR probes and the bonding techniques that may be used to prepare the probes of the present invention are listed in Table 1.

TABLE I

| Synthetic route | Product structure |
|---|---|
| | Membrane Impermeant Moiety / Arm / Reporter group |
| A. via N—oligosaccharide alkyl dicarboxylic acid dihydrazide intermediate followed by: 1. Nucleophilic substitution | a., b., c., d., e. (structures shown) |

TABLE I-continued
| | Product structure | | |
|---|---|---|---|
| Synthetic route | Membrane Impermeant Moiety | Arm | Reporter group |
| | f. 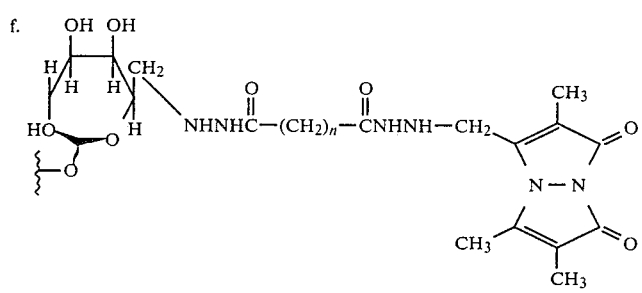 | | |
| | g. 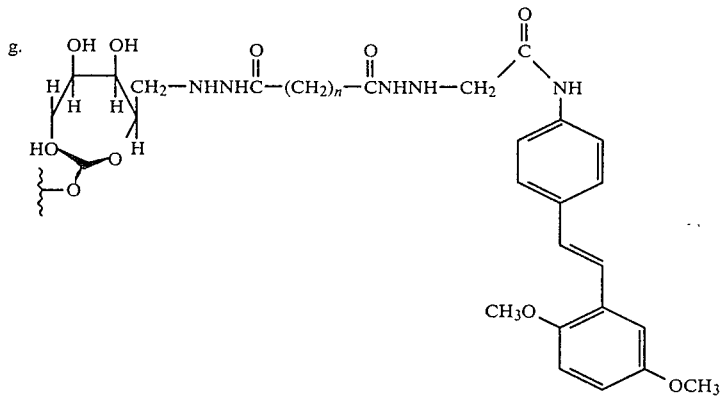 | | |
| | h. 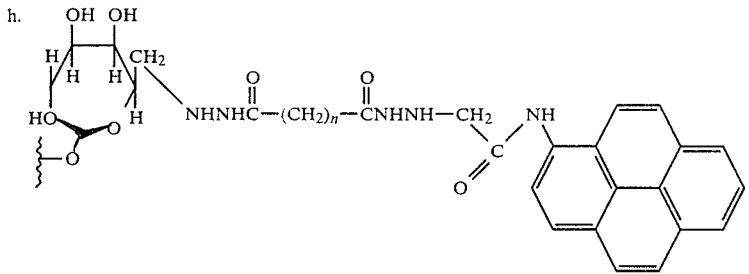 | | |
| 2. carbodiimide coupling | i. 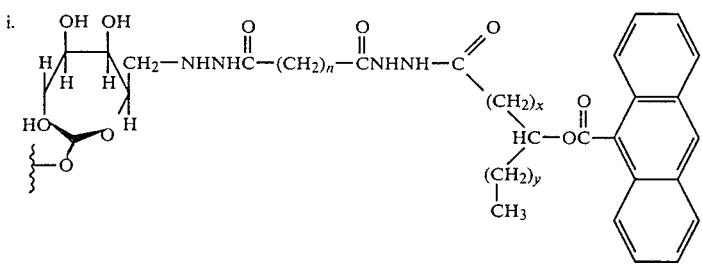 | | |

TABLE I-continued
| | Product structure | | |
|---|---|---|---|
| Synthetic route | Membrane Impermeant Moiety | Arm | Reporter group |
j. 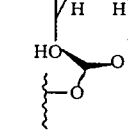
k. 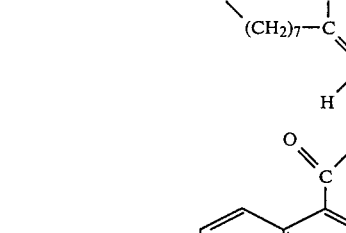
l. 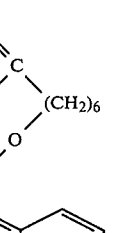
m. 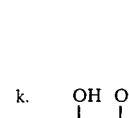
n. 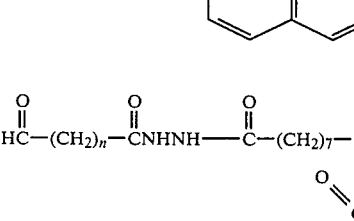

TABLE I-continued

| | Product structure | | |
|---|---|---|---|
| Synthetic route | Membrane Impermeant Moiety | Arm | Reporter group | o. Sugar-CH$_2$-NHNHC(O)-(CH$_2$)$_n$-C(O)NHNH-C(O)-(CH$_2$)$_5$-NH-(4-nitroso-2,1,3-benzoxadiazol-7-yl)

p. Sugar-CH$_2$-NHNHC(O)-(CH$_2$)$_n$-C(O)NHNH-C(O)-(CH$_2$)$_{11}$-N(CH$_3$)-(4-nitro-2,1,3-benzoxadiazol-7-yl)

q. Sugar-CH$_2$-NHNHC(O)-(CH$_2$)$_n$-C(O)NHNH-C(O)-(CH$_2$)$_x$-pyrenyl r. Sugar-CH$_2$-NHNHC(O)-(CH$_2$)$_n$-C(O)NHNH-C(O)-CH=CH-pyrenyl s. Sugar-CH$_2$-NHNHC(O)-(CH$_2$)$_n$-C(O)NHNH-C(O)-(CH$_2$)$_7$-CH=CH-CH=CH-CH=CH-CH$_2$CH$_3$ TABLE I-continued

| | Product structure | | |
|---|---|---|---|
| Synthetic route | Membrane Impermeant Moiety | Arm | Reporter group |
| | t. | (structure) | |
| | u. | (structure) | |
| 3. reaction with activated esters | v. | (structure) | |
| | w. | (structure) | |
| | x. | (structure) | |

TABLE I-continued

| | Product structure | | |
|---|---|---|---|
| Synthetic route | Membrane Impermeant Moiety | Arm | Reporter group | y. [structure: sugar-CH₂-NHNHC(O)-(CH₂)ₙ-C(O)NHNH-C- attached to TEMPO-like nitroxide with CH—CH₂ bridge, four CH₃ groups, N-O•]

4. reaction with isothiocyanates z. [structure: sugar-CH₂-NHNHC(O)-(CH₂)ₙ-C(O)NHNH-C(S)-NH-pyrene]

aa. [structure: sugar-CH₂-NHNHC(O)-(CH₂)ₙ-C(O)NHNH-C(S)-NH-phenyl-coumarin derivative with CH₃ group and N(CH₂CH₃)(CH₂CH₃) diethylamino group]

5. Schiff's base formation with carbonyl compounds followed by borohydride reduction bb. [structure: sugar-CH₂-NHNHC(O)-(CH₂)ₙ-C(O)NHNH-CH₂-pyrene]

cc. [structure: sugar-CH₂-NHNHC(O)-(CH₂)ₙ-C(O)NHNH-CH₂-anthracene]

B. Thiol addition to I—pyrene-maleimide

TABLE I-continued

| | Product structure | | |
|---|---|---|---|
| Synthetic route | Membrane Impermeant Moiety | Arm | Reporter group |
| 1. reaction of glutathione | dd. | | |
| 2. reaction of glutathione-maleimide derivative (Cogan & Schachter, 1981) | ee. | | |
| C. Schiff's base formation of pyrene alkanoyl hydrazide with galactose oxidase treated oligosaccharides; borohydride reduction | ff. | | |

Names of compounds a. 4-(N—oligosaccharide alkyl dicarboxylic acid dihydrazino)-(7-nitrobenzo-2-oxa-1,3-diazole)
b. 4-(N—oligosaccharide alkyl dicarboxylic acid dihydrazino)-methyl-7-methoxycoumarin
c. 4-(N—oligosaccharide alkyl dicarboxylic acid dihydrazino)-methyl-7-hydroxycoumarin
d. 9-(N—oligasaccharide alkyl dicarboxylic acid dihydrazino)-acridine
e. 2-(N—oligosaccharide alkyl dicarboxylic acid dihydrazino)-ethylamino(7-nitrobenzo-2-oxa-1,3-diazol-4-yl)
f. 4-(N—oligosaccharide alkyl dicarboxylic acid dihydrazino)methyl-3,6,7-trimethyl-1,5-diazabicyclo[3.3.0]octa-3,6-diene-2,8-dione
g. 2,5-dimethoxystilbene-4'-(N—oligosaccharide alkyl dicarboxylic acid dihydrazino)acetamide
h. N—(1-pyrene)-(N'—oligosaccharide alkyl dicarboxylic acid dihydrazino)acetamide
i. N—(ω-carbo-oligosaccharidehydrazino)acryl-N'—(9-anthroyloxy)acylhydrazine
j. N—(ω-carbo-oligosaccharidehydrazino)acyl-N'—16-(9-anthroyloxy)palmitelaidylhydrazine
k. N—(ω-carbo-oligosaccharidehydrazino)acyl-N'—12-(9-anthroyloxy)oleoylhydrazine
l. N—(ω-carbo-oligosaccharidehydrazino)acyl-N'—(7-hydroxycoumarin-4-yl)acetylhydrazine
m. N—(ω-carbo-oligasaccharidehydrazino)acyl-N'—(7-hydroxycoumarin-3-yl)acetylhydrazine
n. N—(ω-carbo-oligosaccharidehydrazino)acyl-N'—(7-dimethylaminocoumarin-4-yl)acetylhydrazine
o. N—(ω-carbo-oligosaccharidehydrazino)acyl-N'—[6-N''—(7-nitrobenzo-2-oxa-1,3-diazol-4-yl)aminohexanoyl]hydrazine

TABLE I-continued

| | Product structure | | |
|---|---|---|---|
| Synthetic route | Membrane Impermeant Moiety | Arm | Reporter group |
| p. N—(ω-carbo-oligosaccharidehydrazino)acyl-N'—[12-N"—methyl-N"—(7-nitrobenzo-2-oxa-1,3-diazol-4-yl)aminododecanoyl]hydrazine | | | |
| q. N—(ω-carbo-oligosaccharidehydrazino)acyl-N'—ω-(pyren-1-yl)acylhydrazino | | | |
| r. N—(ω-carbo-oligosaccharidehydrazino)acyl-N'—3-(pyren-1-yl)propenoylhydrazine | | | |
| s. N—(ω-carbo-oligosaccharidehydrazino)acyl-N'—cis-parinaroylhydrazine | | | |
| t. N—(ω-carbo-oligosaccharidehydrazino)acyl-N'—trans-parinaroylhydrazine | | | |
| u. N—(ω-carbo-oligosaccharidehydrazino)acyl-N'—doxylacylhydrazine | | | |
| v. N—(ω-carbo-oligosaccharidehydrazino)acyl-N'—anthraniloylhydrazine | | | |
| w. compound q | | | |
| x. compound p | | | |
| y. N—(ω-carbo-oligosaccharidehydrazino)acyl-N'—(2,2,5,5-tetramethyl-3-pyrrolidin-1-oxyl-carbo)hydrazine | | | |
| z. 1-(ω-carbo-oligosaccharidehydrazino)acyl-4-(pyren-1-yl)-3-thiosemicarbazide | | | |
| aa. 1-(ω-carbo-oligosaccharidehydrazino)acyl-4-[3'-(4"-phenyl)-7'-diethylamino-4'-methylcoumarin]-3-thiosemicarbazide | | | |
| bb. 1-(N'—oligosaccharide alkyldicarboxylic acid dihydrazino)-methylpyrene | | | |
| cc. 9-(N'-oligosaccharide alkyldicarboxylic acid dihydrazino)-methylanthracene | | | |
| dd. Glutathione-pyrene I | | | |
| ee. Glutathione-pyrene II | | | |
| ff. N—oligosaccharide(pyren-1-yl)butyrylhydrazide | | | |

Although the impermeant spectroscopic probes of the present invention are useful in the elucidation of many structure-function relationships, many of them are particularly suited to quantitative studies of membrane lipid fluidity. The term "lipid fluidity" as used herein incorporates, inter alia, the relative motional freedom of the lipid molecules or substituents thereof, combining the concepts of both the rate and the extent of molecular movement.

It may be noted that because the spectroscopic probes of the present invention are membrane impermeant, in situ studies with intact cells can be undertaken with the assurance that the fluorescent signal relates only to the plasma membrane. Information is thus obtained about a subcellular fraction (the plasma membrane) without the need for prior isolation and purification, a process that is time consuming, may introduce artifacts and is not by current methodology practical in many cases. Among others, the following studies are particularly amenable by the techniques of the present invention.

(a) Estimation of hemileaflet fluidity. Whole cells in suspension are treated with the impermeant probe, which intercalates in the outer leaflet alone. Determination of the polarization of fluorescence or electron spin resonance (ESR) signal provides an index of the rotational diffusion or motional freedom of the probe in the exofacial leaflet. Subsequently, the cells are lysed and probe introduced into the endofacial leaflet as well. Comparison of the fluorescence polarization or ESR signal observed with the probe in the outer as compared to both leaflets permits assessment of the fluidity of each leaflet.

(b) Single cell studies. The fluidity of the outer leaflet of a single cell can be assessed with an impermeant fluorophore by means of fluorescence polarization microscopy. A fluorescence microscope with excitation and emission polarizers and a photometer to quantify the emitted fluorescent light is readily available commercially. Since the NBD fluorophores are excited and emit in the visible spectrum, quartz optics are not required. Moreover, the potential damaging effects of short-wavelength irradiation of the cells is avoided. Neoplastic cells often show altered membrane fluidity as contrasted to the non-neoplastic precursor cells. Quantitative measurements thus obtained may be useful in differential diagnosis and provide a useful record for medico-legal purposes.

Evaluation of the inner (endofacial) leaflet fluidity of such cells is also possible if the cells are first rendered permeable, e.g., by osmotic lysis.

(c) Lateral diffusion. In combination with the method of fluorescence photobleach recovery, the impermeant NBD fluorophores can be used to estimate coefficients of lateral diffusion in plasma cell membranes of intact cells. In contrast to measurements obtained by prior art techniques, the probes of the present invention yield diffusion coefficients specific to the outer hemileaflet of the cells. Since the hemileaflets are known to differ in lipid composition, selective assessment of the fluidity is essential to an understanding of the functional significance of the membrane lipids.

It may be further noted that there is increasing evidence that fundamental cellular processes such as neoplastic transformation, cell fusion and transmembrane transduction of signals are influenced markedly by membrane lipid fluidity. Moreover, different cell types exhibit different and characteristic membrane fluidity values. The application of the fluorescence microscopy techniques using the impermeant probes of the present invention provide data for pathologists and clinicians in the identification and differentiation of specific cell types, particularly of neoplastic versus non-neoplastic cells, and of highly malignant versus less malignant cells.

Having generally described the invention, a more complete understanding can be obtained by reference to certain specific examples, which are provided herein for purposes of illustration only and are not intended to be limiting unless otherwise specified.

DESCRIPTION OF THE PREFERRED EMBODIMENTS

Preparation of Oligosaccharide Derivatives

The structures of pyrene-linked derivatives of lactose, raffinose, and stachyose are illustrated in FIG. 2. For the preparation of these compounds, the terminal galactose residue of each sugar was oxidized enzymatically at the C6(-CH$_2$OH) position to an aldehyde and treated with pyrenebutyryl hydrazide (PBH) to form a Schiff's base, which was then reduced with borohydride to yield the oligosaccharide-substituted hydrazide.

In a typical preparation, 49.5 μmol of the oligosaccharide was dissolved in 1.25 mL of 0.1 M potassium phosphate, pH 6.0. Approximately 10 units of *Dactylium dendroides* galactose oxidase (EC 1.1.3.9, Worthington Biochemical Corp.) dissolved in 1.25 mL of water and approximately 180 units of catatase (E.C. 1.11.1.6, Sigma Chem. Co., from bovine liver) were added, and the solution was stirred gently for 30 min at room temperature. The pH was then lowered to 5.6 with 0.1 N HCl and 16.5 μmol of 4-(1-pyrene)butyryl hydrazide (Molecular Probes, Inc., Plano, TX) dissolved in 2.5 mL of tetrahydrofuran added. The reaction mixture was stirred at 37° C. for 2 h and then overnight at room temperature. For reduction of the Schiff's base, the pH was raised to 8.3 with 1 N NaOH, 3.75 mg of $NaBH_4$ dissolved in 0.1 mL of ice-cold $H_2O$ was added, and the mixture was stirred for 30 min at room temperature and then 4 hours at 4° C. The pH was lowered to 5 with glacial acetic acid and the material concentrated on a rotary evaporator (40°–45° C.) to 150–300 μL. The reaction yields were usually greater than 90%. The products were purified by thin-layer chromatography on 1-mm-thick silica gel plates (Brinkmann Instruments, Inc., SIL G-100 UV 254). Each plate was developed initially in $CHCl_3/CH_3OH$ solution (9/1 v/v) to remove unreacted PBH from the reaction product, which remained at the origin. After the plate dried, it was developed in the same direction in n-butyl alcohol/glacial acetic acid/water (4/1/2 v/v/v). In this solvent system, each of the pyrenebutyryl hydrazide derivatives of lactose (LPBH), raffinose (RPBH), and stachyose (SPBH) moved as a major fluorescent band with $R_f$ values of 0.78, 0.35, and 0.20, respectively. Each fluorescent band was scraped and desorbed from the silica by three successive washes with 2 mL of ice-cold water. Nonfluorescent impurities extracted from the silica were removed by adsorbing the product on a small reverse-phase chromatography column (SEP-PAK $C_{18}$, Waters Associates, Milford, MA) followed by elution with $CH_3OH/H_2O$ (3/1 v/v). Most of the methanol was then evaporated under a $N_2$ stream at room temperature, the final product was lyophilized and dissolved in an isotonic "wash" buffer (30 mM sodium phosphate, pH 7.4, 117 mM NaCl, and 2.8 mM KCl) to give a final concentration of 0.5–2.0 mM in terms of pyrene, and the stock solutions were stored frozen at $-20°$ C. Assay of the products yielded pyrene/oligosaccharide molar ratios of 0.85–1.1 for various preparations of LPBH, RPBH, and SPBH. Preparations of SPBH were also purified by high-pressure liquid chromatograhy using a reverse-phase $C_{18}$ column (Waters Associates) and a linear gradient of $CH_3OH$ in $H_2O$ (50–100%, v/v). The results were similar with SPBH purified by either thin-layer or high-pressure liquid chromatography.

Preparation of Glutathione Derivatives

The structures of two pyrene-linked derivatives of glutathione are also illustrated in FIG. 2. Compounds I and II differ in the length of the connecting arm and are termed, respectively, glutathione-pyrene I (GS-PI) and II (GS-PII). For preparation of GS-PI, 0.2 mmol of N-(1-pyrenyl)maleimide (Molecular Probes, Inc.) was dissolved in 25 mL of ethanol/acetone (1/1 v/v). To this solution were added 5 mL of 0.1 M $NaHCO_3$ followed by 0.23 mmol of glutathione (Sigma Chemical Co.) dissolved in 20 mL of water, the pH adjusted to 7.0 with 1 N NaOH, and the reaction mixture incubated under argon at 37° C. for 90 minutes. Alkylation of the glutathione (GSH) was complete as judged by the disappearance of the SH group and the appearance of fluorescence, since unreacted pyrenylmaleimide does not fluoresce. The mixture was evaporated to dryness in a rotary evaporator at 35°–40° C., the residue dissolved in glacial acetic acid, and the product precipitated by addition of acetone and chilling to $-15°$ C. The pellet obtained on centrifugation was reprecipitated once as just described and the resulting pellet dissolved in water and purified further by thin-layer chromatography, as detailed in the preceding section. After development in the n-butyl alcohol/glacial acetic acid/water system, the material gave a major fluorescent band corresponding to $R_f=0.24$. Following elution (see above), the pyrene/glutathione molar ratio in the product varied from 0.94 to 1.14 in various batches.

For the preparation of glutathione-pyrene II, glutathione-maleimide I, prepared as described by Abbott & Schachter, J. Biol. Chem. 251: 7176, 1976 and incorporated herein by reference, was treated with excess ethanedithiol and subsequently with pyrenylmaleimide as follows. A solution was prepared of 3.7 mmol of 1,2-ethanedithiol (Aldrich Chemical Co.) in 10 mL of ethanol/tetrahydrofuran/water (1.1/1.8/2.1 v/v/v). A second solution of 0.37 mmol of glutathione-maleimide I in 5 mL of 50% ethanol was prepared, adjusted to pH 7 with 1N NaOH, and added to the ethanedithiol dropwise, with vigorous stirring, over a period of 10 minutes at room temperature. After being stirred for an additional 40 minutes at room temperature, the mixture was extracted 5 times with 4 volumes of $CHCl_3$ to remove excess ethanedithiol, and the last $CHCl_3$ extract showed negligible —SH. The residual aqueous phase, approximately 8 mL, was diluted to 24 mL with water and the pH adjusted to 6.8 with 1 M $NaHCO_3$. To it were added 24 mL of a solution of 0.26 mmol of N-(1-pyrenyl)maleimide in ethanol/acetone (1/1 v/v), and the reaction mixture was shaken overnight under argon, at room temperature, in a vessel shielded from light. Subsequent purification followed the procedures described for GS-PI. Thin-layer chromatography in the n-butyl alcohol/glacial acetic acid/water system revealed three major fluorescent products corresponding to $R_f$ values of 0.35, 0.37, and 0.40. After elution, the fraction of the total bound pyrene recovered in each band was, respectively, 0.32, 0.31 and 0.37, and the pyrene/glutathione molar ratio was 1.13, 0.98, and 1.13, respectively. The products appear to be closely related structures which may be stereoisomers, inasmuch as each succinimidyl ring in the GS-PII structure, (FIG. 2) contains one asymmetric carbon linked to sulfur. The three chromatographically pure bands were used separately in the membrane experiments but yielded similar results.

Derivatives similar to GS-PI and GS-PII were also made by using N-(1-pyrenyl)iodacetamide (Molecular Probes, Inc.) in place of pyrenylmalemide. Results obtained in erythrocyte experiments with the iodacetamide derivatives were comparable to those observed with the foregoing compounds.

N-Oligosaccharide-alkyldicarboxylic acid dihydrazide impermeant Probes

As shown in the reaction scheme in FIG. 3 the C6 alcohol of the terminal galactose residue of an oligosaccharide was converted enzymatically to an aldehyde (Eq. 1a, b, c in FIG. 3), treated with an excess of an alkyldicarboxylic acid dihydrazide (Eq. 2 in FIG. 3)

and the Schiff's base thus formed reduced with sodium borohydride to yield the mono-oligosaccharide substituted alkyldicarboxylic acid dihydrazide. The preparation of N-stachyosyl-succinic acid dihydrazide, compound I (FIG. 4) is typical for this new family of oligosaccharide alkyldicarboxylic acid dihydrazides and its method of preparation is described hereunder in detail.

Following the method of Cogan and Schachter (1981), *Biochemistry* 20: 6396-6403 and incorporated herein by reference, to 73.8 mg (100 μmoles) stachyose tetrahydrate (Sigma Chemical Co.) dissolved in 2.5 ml 0.1 M potassium phosphate, pH 6.0, were added 33 units galactose oxidase (Sigma, E.C. 1.1.3.9; Type V from *Dactylium dendroides*) in 2.5 ml H$_2$O and 360 units of catalase (Sigma, E.C. 1.11.16 from bovine liver), and the solution was stirred at room temperature for 2 hrs. The pH was decreased to 5.6 with 0.1 N HCl, 40 mg (274 μmoles) succinic acid dihydrazide in 4.0 ml of 0.5M sodium acetate buffer, 5.6, added and the reaction mixture incubated for 2 hrs at 37° and then at room temperature for 15 hrs. The pH was raised to 8.3 with 1.0 N NaOH and 24 mg (634 μmoles) NaBH$_4$ dissolved in 0.2 ml ice cold H$_2$O added. After the reaction mixture was stirred for 30 min. at room temperature and for 4 hrs at 4°, the excess borohydride was decomposed by addition of acetic acid until the pH was 5. The solution may be stored at −20° C. Removal of excess unreacted dihydrazide and partial purification was achieved after concentrating the solution 2-3 fold at reduced pressure on a rotary evaporator (<40° C.) by gel filtration through BioGel P-2 (bed volume: 100 ml; eluent: 0.05 M sodium phosphate, pH 6.5). Assaying the fractions (1.2 ml) for carbohydrate (phenol/sulfuric acid) and hydrazide (trinitrobenzenesulfonic acid, 3 mg/ml in 0.05 M sodium phosphate, pH 6.5) showed an initial peak containing both sugar and hydrazide separated from a second peak containing only hydrazide. Combination of those fractions (33-36) containing both sugar and hydrazide yielded 60 μmoles (60%) N-stachyosylsuccinic acid dihydrazide.

Substituting different dihydrazides and/or oligosaccharides in the above procedure yields other N-oligosaccharide-alkyl-dicarboxylic acid dihydrazides. The following preparations have been made (oligosaccharide, dihydrazide): stachyose, succinic acid dihydrazide; stachyose, adipic acid dihydrazide; raffinose, succinic acid dihydrazide; lactose, succinic acid dihydrazide. Longer chain length dihydrazides (e.g., n=8 or 10; eq. 2, FIG. 3) may also be used, thereby adjusting the depth of penetration of the spectroscopic reporter group and the hydrophobic/hydrophilic balance in the final product.

Coupling of the N-oligosaccharide-alkyldicarboxylic acid dihydrazide intermediates to the spectroscopic reporter groups may be achieved by (1) nucleophilic substitution reactions, (2) carbodiimide coupling, or (3) other methods, including Schiff's base formation and borohydride reduction. Purification of the final products is accomplished by thin-layer chromatography, high-pressure liquid chromatography or gel filtration. Several examples follow. 1. Nucleophilic substitution (a) To 18.7 μmoles N-stachyosyl adipic acid dihydrazide in 3 ml 0.05M sodium phosphate, pH 6.5, is added 187 μmoles 4-chloro-7-nitrobenzo-2-oxa-1, 3-diazole (NBD-4-yl chloride) in 1.2 ml of tetrahydrofuran (THF) and the reaction mixture allowed to stand for 24 hrs at room temperature. Purification via gel filtration (Sephadex G-15, 30 ml bed volume, 25% MeOH) gave the N-stachyosyl-N'-(NBD-4-yl) adipic acid dihydrazide (absorbance max, 455 nm), estimated at greater than 90% fluorescent purity as shown by silica gel thin layer chromatography (TLC) (solvent 1: CHCl$_3$/MeOH, 9/1, v/v; solvent 2: n-BuOH/HOAc/H$_2$O, 4/1/2,v/v/v (Cogan & Schachter (1981), R$_f$=0.15).

(b) Similarly, other fluorescent groups with electrophilic centers may be used, as for example: N-(NBD-4yl)-aziridine; monobromobimane; 4-bromomethyl-7-methoxycoumarin; 4-chloromethyl-7-hydroxycoumarin; 9-chloroacridine; 2,5-dimethoxystilbene-4'-iodoacetamide; N-(1-pyrene)iodoacetamide.

2. Carbodiimide coupling (a) To 10 μmoles N-stachyosyl-succinic acid dihydrazide (SSAD) in 1.0 ml 0.05 M sodium phosphate, pH 6.5, is added 10 μmoles 12-(9-anthroyloxy)-stearic acid (12-AS) in 1.0 ml tetrahydrofuran (THF) and the pH adjusted to 4.0 with 1.0 N HCl. The solution is protected from light, cooled to 0°, and 10 mg (52 μmoles) 1-(3-dimethylaminopropyl)-3-ethylcarbodiimide hydrochloride (Aldrich, water-soluble diimide) added. After 30 min another 10 mg of water soluble diimide were added and the solution allowed to warm to room temperature. After an additional 30 minutes a final 10 mg portion of the carbodiimide was added and the solution allowed to remain at room temperature, protected from light, overnight. The THF was removed under a stream of N$_2$, the resulting suspension centrifuged in a clinical centrifuge (350g), and the supernatant removed from the water insoluble material (mostly 12-AS by TLC). Preparatory silica gel TLC, developing first with solvent 1 and then with solvent 2 (see above), provided the N-[3-carbostachyosehydrazino]propionyl-N'-12-(9-anthroyloxy)stearoyl hydrazine as a fluorescent material with R$_f$=0.3.

(b) In similar procedures the 2- and 7-anthroyloxy-stearates (2-AS and 7-AS) have been coupled via water soluble carbodiimide to SSAD. Other anthroyloxy derivatives of saturated and unsaturated fatty acids may also be used.

(c) Similarly, the coupling of fluorescent reporters based on coumarin, 4-amino-7-nitrobenzo-2-oxa-1, 3-diazole, pyrene, parinaric acid (cis and trans) may be achieved via the respective carboxylic acids, such as 7-hydroxycoumarin-4-acetic acid; 7-hydroxycoumarin-3-carboxylic acid; 7-dimethylaminocoumarin-4-acetic acid; 6-N-(NBD-4-yl)aminohexanoic acid; 12-N-methyl-N-(NBD-4-yl)aminododecanoic acid; pyrene-1-carboxylic acid; 3-(1-pyrene)propenoic acid, pyrenebutyric, pyrenedecanoic, pyrenedodecanoic, and pyrenehexadecanoic acids; cis and trans parinaric acids.

(d) Similarly, electron spin resonance (ESR) reporters may be coupled to these N-oligosaccharide-alkyl-dicarboxylic acid dihydrazide intermediates via water soluble carbodiimides, using the various N-oxyl-4,4-dimethyloxazolidine ("doxyl") derivatives of ketostearic acid (e.g., 5-doxylstearic acid; 12-doxylstearic acid) and other "doxyl"-substituted fatty acids.

3. Other substitution and addition methods (a) Activated esters: N-oligosaccharide-alkyldicarboxylic acid dihydrazides will react with activated esters to yield the stable mixed di-acylhydrazines, as in the reaction of SSAD with p-nitrophenyl anthranilate, N-hydroxy succinimidyl-10-(1-pyrene)decanoate, and N-hydroxy succinimidyl-12-N-methyl-N-(NBD-4-yl)aminododecanoate for fluorescent probes and N- hydroxy succinimidyl-2,2,5,5-tetramethyl-3-pyrrolin-1-oxyl-3-carboxylate for ESR probes.

(b) Isothiocyanates: N-oligosaccharide-alkyldicarboxylic acid dihydrazides will react with isothiocyanates to yield the stable N-acylthiosemicarbazides as in the reaction of SSAD with 1-pyreneisothiocyanate and 3-(4-isothiocyanatophenyl)-7-diethyl-amino-4-methylcoumarin.

(c) Carbonyl compounds: N-oligosaccharide-alkyldicarboxylic acid dihydrazides will react with aldehydes and ketones to yield Schiff's bases which, following $NaBH_4$ reduction give the disubstituted alkyldicarboxylic acid dihydrazides. 1-Pyrene-carboxyaldehyde and 9-anthraldehyde are examples of fluorescent aldehydes that may be used in this manner. The procedure using 9-anthraldehyde follows.

To 50 μmoles N-stachyose-adipic acid dihydrazide in 10 ml 0.05M sodium phosphate, pH 5.2, were added 11 mg (52 μmoles) 9-anthraldehyde in 3 ml THF. After the addition of 3 ml ETOH to give an almost clear solution, the reaction mixture was kept at 37° for 3 hrs and room temperature overnight. The pH was adjusted to 8.1 with 1N NaOH and 60 mg (1.6 mmoles) sodium borohydride dissolved in 0.5 ml ice cold $H_2O$ added, the reaction stirred 2 hours at room temperature and then excess borohydride decomposed by the dropwise addition of acetic acid until the pH was 5.6. Organic solvents were removed on the rotary evaporator at reduced pressure ($<40°$ C.) and the solution frozen and lyophilized. The dry powder was suspended in 25% MeOH and centrifuged at 350 g to remove insoluble material. A portion of the supernatant was passed through a C-18 Sep-Pak (Waters Associates) and then put through a Bio-Gel P-2 column (eluent: 25% MeOH; bed volume: 30 ml); 1 ml fractions were collected, monitored by TLC, and fractions 22-27 (containing the major, slow moving fluorescent product [$R_f$ 0 in solvent I; $R_f$ 0.3 in solvent 2] combined and lyophilized. This material was completely soluble in 8 mM sodium phosphate, pH 7.4 containing 145 mM NaCl and 5 mM KCl. Assay revealed an anthracene/stachyose ratio of 0.9.

Intact Erythrocyte Studies

Human erythrocytes separated by centrifugation from the freshly drawn blood of normal donors or from recently outdated blood-bank blood were washed by centrifugation 3 times with the isotonic "wash buffer" to remove plasma components and buffy coat. For assessment of the outer hemileaflet, intact erythrocytes were treated with GS-PI or GS-PII, and the fluorescence of the cell suspensions was determined directly, as follows.

Washed cells suspended to a hematocrit of 1.0% in wash buffer were incubated with shaking in the presence of 200-400 μM fluorophore for 60 min at 37° C. The cells were then pelleted by centrifugation at 2000g for 10 min and washed 4 times with 10 mL (2000 volumes) of wash buffer. Cells were finally diluted with wash buffer to a hematocrit of 0.05%, and the polarization of fluorescence was estimated as described below. Control cell suspensions prepared identically in the absence of fluorophore were used to correct for light scattering. Under the conditions of measurement, the scattering corrections amounted to 25-30% of the fluorescence signals. While these exceed the scattering corrections of 2-10% that we observe routinely with ghost membrane suspensions, the fluorescence anisotropy values of the intact cell suspensions were highly reproducible and did not vary significantly with dilution to hematocrit values of 0.01-0.02%.

The following procedure obviates the larger scattering corrections applicable to the cell suspensions, while it yields fluorescence anisotropy values for the outer hemileaflet which are quite similar to those observed directly with intact erythrocytes. Washed cells suspended to a hematocrit of 20% in wash buffer are incubated with shaking in the presence of 10-400 μM impermeant fluorophore. After 60 minutes at 37° C., the suspensions are pelleted and washed 4 times as described above, and the final pellets are lysed by suspension in 200 volumes of cold (2°-5° C.) 5 mM sodium phosphate, pH 8.0. The ghosts are washed 3 times by centrifugation (30,000 g, 15 minutes) in 200 volumes of the cold 5 mM sodium phosphate to yield membranes essentially free of hemoglobin and suitable for fluorescence mesurements as described below. Preparations were maintained at 2°-5° C. to minimize possible redistribution of the impermeant probes to the inner leaflet. The fluorescence anisotropy and excimer estimations to be described suggest that relatively little redistribution is evident at 2°-5° C. for as long as 12 h. This may be a consequence of the relatively high partition coefficients, (membrane lipid)/(suspending medium water), observed for all probes tested. Values for these coefficients, defined as (moles of probe per gram of membrane lipid)/(moles of probe per gram of water), approximated $10^5$ (range of $0.4 \times 10^5 - 12 \times 10^5$).

Ghost Membrane Studies

Both the inner and outer membrane leaflets were labeled by preparing ghost membranes from washed erythrocytes and suspending them in either 5 mM sodium phosphate, pH 8.0, or wash buffer to a membrane protein concentration of approximately 1 mg/mL. Impermeant fluorophore was added as described above, the suspensions were shaken for 60 minutes at 37° C., and the loaded membranes were harvested and washed 3 times with 200 volumes of cold 5 mM sodium phosphate. These suspensions as well as the membranes obtained after loading the intact cells were adjusted to a protein concentration of 150-200 μg/mL for fluorescence readings.

Intact cells and ghost membranes were loaded with the permeant fluorophores pyrene or 10-(1-pyrene)-decanoic acid (Molecular Probes, Inc.) as described above except that the compounds were dissolved in absolute ethanol and added to the suspensions to yield a final ethanol concentration of 1% (v/v). Control suspensions were treated with ethanol alone.

Liposome Studies

Ghost membranes prepared as described above were extracted by the method of Folch et al., J. Biol. Chem. 226: 497 (1957) and incorporated herein by reference. The dried, extracted lipid was suspended in wash buffer to a final concentration of 3-4 mg/mL. By use of a Branson sonifer (Branson Sonic Power Co., Model 350), the suspensions were sonicated under $N_2$ for 5 minutes at 5° C. and for an additional 5 minutes while the temperature increased to 30° C. After centrifugation at 20,000 g for 30 min, the supernatant dispersions (liposomes) were labeled by incubation with 25-100 μM fluorophore for 60 minutes at 37° C. Labeled liposome membranes were separated from unbound probe in the aqueous medium by gel filteration at 25° C. through a column of Bio-Gel P-4 (Bio-Rad Laboratories). Both labeled and unlabeled dispersions were used for fluorescence studies.

Fluorescence Studies

Excitation and emission spectra (5-nm resolution) and estimations of total fluorescence intensity were obtained with a Perkin-Elmer MFP 2A spectrofluorometer. Steady-state fluorescence polarization measurements were made in an SLM polarization spectrofluorometer, as described by Shachter & Shinitzky, J. Clin. Invest. 59: 536 (1977) and incorporated herein by reference, by using a 1-cm light path and the peak excitation wavelengths shown in Table 2 and 338 and 345 nm, respectively, for pyrene and pyrenedecanoic acid. Emitted light was passed through a Corning 3-75 filter. In all fluorescence measurements, the contribution of scattered light was subtracted. For polarization measurements, the suspension densities were standardized and minimized to avoid depolarization owing to the particulates.

was estimated and compared to reference standards of each probe in 1% $NaDodSO_4$ or added incrementally to each sample. The lipids and proteins of the erythrocyte membrane were considered to be equal in mass and the partial specific volume of the lipids was taken as 1.

Other Methods and Materials

Absorption spectra were recorded in a Cary Model 15 Spectrophotometer. The major extrinsic proteins of the endofacial surface of the erythrocyte membrane, i.e. erythrocyte spectrin and actin (Coomassie brilliant blue bands 1, 2, and 5), were extracted by treatment with 0.1 mM EDTA at pH 8.0, as previously described by Steck & Yu, J. Supramol. Struct. 1:220, 1973 and incorporated herein by reference. At least 60–70% of these proteins were removed as judged by $NaDodSO_4$-polyacrylamide gel electrophoresis. The sugar content of the oligosaccharide derivatives was estimated by the phenol-sulfuric acid method described by Dubois et al. Anal. Chem. 28:350, 1956 and incorporated herein by refer-

TABLE 2

Wavelength Maxima and Limiting Anisotropies of Pyrene Derivatives

| Derivative[a] | $r_0$[b] | medium | excitation | emission monomer | emission excimer |
|---|---|---|---|---|---|
| pyrenebutyrylhydrazide | 0.120 | aqueous[c] | 343 | 378 | |
| | | tetrahydrofuran | 344 | 378 | |
| | | membranes | 349 | 379 | |
| lactose derivative (LPBH) | 0.117 | aqueous | 345 | 379 | |
| | | tetrahydrofuran | 346 | 378 | 468 |
| | | membranes | 347 | 378 | 468 |
| raffinose derivative (RPBH) | 0.119 | aqueous | 345 | 379 | |
| | | tetrahydrofuran | 346 | 378 | 468 |
| | | membranes | 347 | 378 | 468 |
| stachyose derivative (SPBH) | 0.119 | aqueous | 344 | 377 | |
| | | tetrahydrofuran | 346 | 378 | |
| | | hexane | 348 | 387 | 468 |
| | | membranes | 347 | 378 | 468 |
| glutathione-pyrene I | 0.180 | aqueous | 348 | 385 | |
| | | 1-butanol[d] | 360 | 388 | |
| | | membranes | 346 | 377 | |
| glutathione-pyrene II | 0.202 | aqueous | 346 | 377 | |
| | | tetrahydrofuran | 352 | 378 | 464 |
| | | membranes | 348 | 377 | 468 |

[a]Derivatives were tested at concentrations of 2–5 μM.
[b]Maximal anisotropy was determined in propylene glycol at −60° C.
[c]Wash buffer of pH 7.4 (see page 30).
[d]1-Butanol/$H_2O$(96/4 v/v).

The polarization of fluorescence was expressed as the fluorescence anisotropy, r, and the anisotropy parameter, $[(r_0/r) - 1]^{-1}$, was calculated by using values of the maximal limiting anisotropy, $r_0$, determined experimentally for each probe in propylene glycol at −60° C. (Table 2). The anisotropy parameter varies inversely with the fluidity of the microenvironment and directly with ρ, the rotational relaxation time of the fluorophore, according to the Perrin equation $[(r_0/r) - 1]^{-1} = \rho/(3\tau)$, where τ is the mean lifetime of the excited state. The value of τ for each pyrene fluorophore in the erythrocyte membrane was determined experimentally by time-resolved single photon counting (Photo-Chemical Research Associates, London, Ontario; Model 1000 single photon counter), and an apparent rotational relaxation time, ρ′, was calculated from the Perrin equation on the assumption that the depolarizing rotations were unhindered.

The content of each fluorophore in the membrane was estimated fluorometrically. Sodium dodecyl sulfate ($NaDodSO_4$) to a final concentration of 1% (w/v) was added to each suspension and the sample clarified by heating at 100° C. for 3 min. The fluorescence intensity ence, using each oligosaccharide as a standard. Glutathione was estimated by the ninhydrin reaction, Kabat & Mayer, Exptl. Inmunochem. 2nd ed., p. 560, and incorporated herein by reference and protein by the method of Lowry et al. J. Biol. Chem., 193:265, 1951 and incorporated herein by reference, using bovine serum albumin as the standard. The pyrene content of the fluorophores was quantified by optical absorbance in the range 340–342 nm with reference to appropriate standards of pyrenebutyryl hydrazide, pyrenylmaleimide, and pyrenyliodoacetamide.

The results of these studies are noted below.

Spectral Characteristics

Figure 5:
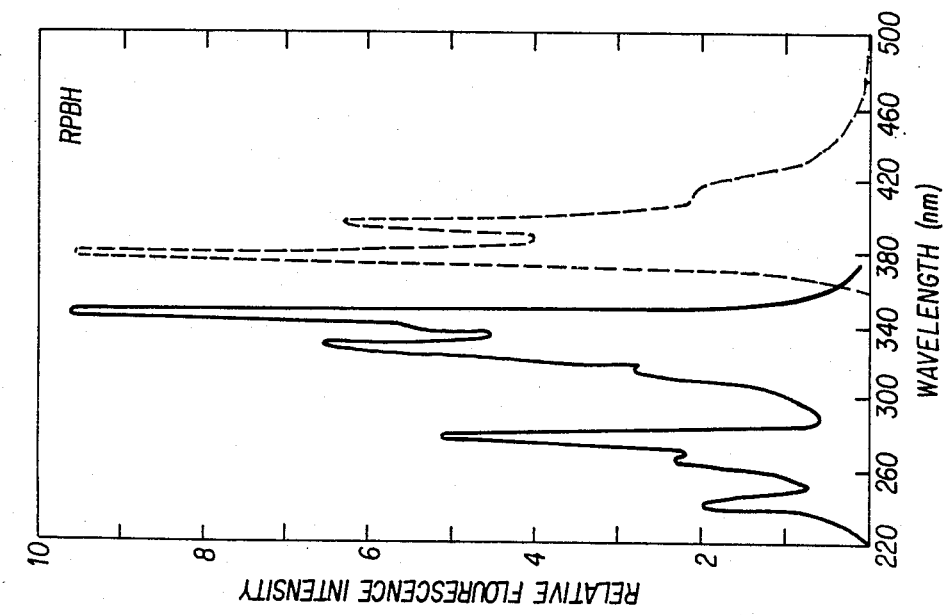
FIG. 5 is a representation of uncorrected excitation (-) and emission (---) spectra of RPBH.

Values for the excitation and emission wavelength maxima of the pyrene derivatives in various solvents and for the maximal limiting anisotropy, $r_0$, in propylene glycol at −60° C. are listed in Table 2. FIG. 5 illustrates excitation and emission spectra of RPBH, which are essentially identical with those of LPBH and SPBH. Although the excitation and monomer emission spectra of all five impermeant derivatives were relatively insensitive to the solvent polarity, a small red shift in the peak excitation wavelength accompanied a decrease in solvent polarity (Table 2). As expected, the excitation maxima of the oligosaccharide derivatives and of GS-PII in situ in the membrane corresponded to the less polar environment. The membrane values for GS-PI, however, did not show a red shift, suggesting that the probe localizes closer to the aqueous interface of the membrane. This conclusion is further supported by the relatively high anisotropy and lack of excimer formation noted below and by the relatively short distance between the glutathione moiety and pyrene in GS-PI (FIG. 2).

The monomer emission spectra of the oligosaccharide derivatives in aqueous buffers were quite similar to that of PBH, but in less polar media such as tetrahydrofuran, tetrahydrofuran-mineral oil mixtures, or hexane, the emission spectra of the impermeant probes showed strong excimer fluorescence, whereas that of PBH did not. The excimer fluorescence observed for the amphipathic probes is probably due to the formation of inverted micelles, with the polar moieties shielded from the solvent.

Fluorescence Anisotropy

The fluorescence anisotropy values observed for the impermeant glutathione derivatives in intact erythrocytes (outer leaflet) as compared to those for leaky ghost membranes (both leaflets) are listed in Table 3. Values for the outer leaflet alone are considerably less than those for the combined leaflets both for GS-PI ($P<0.001$) and for GS-PII ($P<0.02$). Moreover, the anisotropy differences are not ascribable to differences in probe concentration. It is well-known that overlap of the excitation and emission spectra of the pyrene fluorophore can lead to concentration-dependent quenching of fluorescence polarization. The fluorophore concentration in the outer leaflet of the intact cells (Table 2), expressed as the probe/lipid molar ratio, ranged from 0.003 to 0.007, whereas the corresponding range for the combined leaflets of the leaky ghosts was 0.007–0.011.

TABLE 3

Fluorescence Anisotropy of Impermeant Pyrene Derivatives in Intact Erythrocytes and Leaky Ghost Membranes

| derivative | fluorescence anisotropy,[a] r | | P |
|---|---|---|---|
| | erythrocytes | ghosts | |
| glutathione-pyrene I | $0.091 \pm 0.001$ | $0.147 \pm 0.003$ | $<0.001$ |
| glutathione-pyrene II | $0.044 \pm 0.002$ | $0.089 \pm 0.005$ | $<0.02$ |

[a]Values are means ± the standard error (SE) for three different samples of human erythrocytes and ghosts prepared from them.
[P]values for the differences are based on the paired t test.
Anisotropy values were determined at 25° C.

The preceding observation that the fluorescence anisotropy estimated in the outer leaflet is less than that in the inner leaflet is supported further by comparisons of membranes freed of hemoglobin and derived from either intact cell loaded (outer leaflet) or leaky ghost loaded (both leaflets) preparations. In each experiment, intact erythrocytes and leaky ghosts prepared from them were treated initially with various concentrations of impermeant fluorophore, as described supra. Thereafter, washed membranes were prepared from the intact cells and from the leaky ghost loaded preparations, and results of fluorescence anisotropy estimations are shown in Table 4.

TABLE 4

Fluorescence Polarization Studies of Erthrocyte-Loaded and Ghost-Loaded Membranes

| probe | no.[b] | probe/lipid molar ratio, range | fluorescence anisotropy,[a] r | | | anisotropy parameter, $[(r_0/r - 1]^{-1}$ | | |
|---|---|---|---|---|---|---|---|---|
| | | | RBC loaded | ghost loaded | P | RBC loaded | ghost loaded | P |
| GS-PI | 10 | $2 \times 10^{-4} - 3 \times 10^{-3}$ | $0.107 \pm 0.005$ | $0.137 \pm 0.004$ | $<0.001$ | $1.68 \pm 0.19$ | $3.21 \pm 0.35$ | $<0.01$ |
| GS-PII | 24 | $2 \times 10^{-4} - 5 \times 10^{-3}$ | $0.048 \pm 0.001$ | $0.074 \pm 0.002$ | $<0.001$ | $0.31 \pm 0.01$ | $0.59 \pm 0.03$ | $<0.001$ |
| LPBH | 4 | $3 \times 10^{-4} - 2 \times 10^{-3}$ | $0.018 \pm 0.001$ | $0.029 \pm 0.001$ | $<0.01$ | $0.18 \pm 0.01$ | $0.33 \pm 0.01$ | $<0.01$ |
| RPBH | 10 | $3 \times 10^{-4} - 2 \times 10^{-3}$ | $0.014 \pm 0.001$ | $0.023 \pm 0.001$ | $<0.001$ | $0.13 \pm 0.01$ | $0.24 \pm 0.01$ | $<0.001$ |
| SPBH | 12 | $2 \times 10^{-4} - 3 \times 10^{-3}$ | $0.012 \pm 0.001$ | $0.022 \pm 0.002$ | $<0.01$ | $0.11 \pm 0.01$ | $0.23 \pm 0.02$ | $<0.01$ |

[a]Values are means ± SE. P values are based on the paired t test.
[b]Number of erythrocyte-loaded and ghost-loaded preparations examined. Anistropy estimations were at 25° C.

The mean anisotropy values for GS-PI and GS-PII observed in the membranes derived from the intact cell loaded preparations (Table 4) agree closely with the values obtained by direct observation of the intact cells (Table 3); the leaky ghost loaded preparations in Tables 3 and 4 are also essentially identical. Further, the data in Table 4 demonstrate that the pattern of lower fluorescence anisotropy in intact cell loaded as compared to leaky ghost loaded preparations also obtains for three oligosaccharide derivatives. The probe/lipid molar ratios in these experiments were varied from 0.0005 to 0.003 with little effect on the fluorescence anisotropy values and no effect on the consistent differences between the intact cell loaded and leaky ghost loaded preparations. Hence, the characteristic difference in fluorescence anisotropy between the two hemileaflets is not ascribable to concentration-dependent quenching of the fluorescence polarization of any of the impermeant probes.

Figure 6:
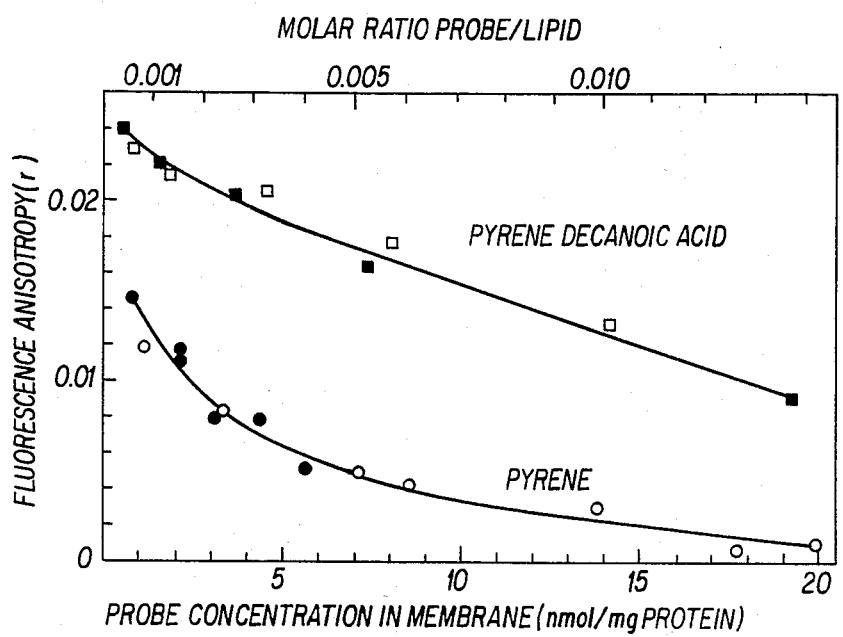
FIG. 6 is a graphical representation of fluorescence anisotropy of pyrene and pyrene decanoic acid in membranes.

The foregoing experiments indicate that impermeant pyrene derivatives inserted into the outer leaflet of the intact erythrocyte retain this selective distribution through subsequent steps of osmotic lysis and the preparation of washed membranes under conditions described supra. Membrane-permeant pyrene fluorophores, on the other hand, would be expected to distribute readily between the two hemileaflets, and the fluorescence anisotropy values would be independent of the route of loading. As a test of this prediction, erythrocytes and leaky ghosts were treated with pyrene or pyrenedecanoic acid, and washed membranes were prepared and tested as described in the preceding paragraph. The results shown in FIG. 6 demonstrate that at a given probe/lipid molar ratio the fluorescence anisotropy value of each probe is independent of the route of loading. The results also illustrate concentration-dependent quenching of the fluorescence polarization of both fluorophores.

The data of Tables 3 and 4 also indicate that values of the fluorescence anisotropy and the anisotropy parameter, $[(r_0/r) - 1]^{-1}$, of GS PI consistently exceed those of GS-PII in comparable preparations. Without subscribing to any particular theory, a possible explanation is that the shorter connecting arm in GS-PI constrains the pyrene moiety to localize in lipid regions which are closer to the aqueous interfaces of the membrane and of lower fluidity.

Excited-State Lifetime Studies

The mean excited-state lifetime, $\tau$, of each impermeant fluorophore in membranes derived from erythrocyte-loaded and ghost-loaded preparations was estimated (Table 5), inasmuch as lifetime differences could underly the differences in fluorescence anisotropy.

TABLE 5

Excited-State Lifetimes in Erythrocyte-Loaded and Ghost-Loaded Membranes

| probe | no. of preparations | probe/lipid molar ratio range | mean lifetime,[a] $\tau$(ns) RBC loaded | mean lifetime,[a] $\tau$(ns) ghost loaded | app rotational relaxation time, p' (ns) RBC loaded (a) | app rotational relaxation time, p' (ns) ghost loaded (b) | P | (b)/(a) ratio |
|---|---|---|---|---|---|---|---|---|
| GS-PI  | 6  | $2 \times 10^{-4} - 6 \times 10^{-3}$ | 103 ± 5 | 97 ± 3  | 519 ± 59 | 933 ± 101 | <0.01  | 1.8 |
| GS-PH  | 10 | $8 \times 10^{-4} - 6 \times 10^{-3}$ | 101 ± 2 | 105 ± 1 | 95 ± 3   | 186 ± 8   | <0.001 | 2.0 |
| LPBH   | 4  | $3 \times 10^{-4} - 2 \times 10^{-3}$ | 124 ± 2 | 122 ± 2 | 69 ± 4   | 120 ± 2   | <0.001 | 1.7 |
| RPBH   | 6  | $4 \times 10^{-4} - 2 \times 10^{-3}$ | 130 ± 1 | 134 ± 1 | 51 ± 6   | 96 ± 5    | <0.001 | 1.9 |
| SPBH   | 4  | $2 \times 10^{-4} - 3 \times 10^{-3}$ | 121 ± 4 | 118 ± 3 | 40 ± 3   | 80 ± 6    | <0.001 | 2.0 |

[a]Values are means ± SE for the indicated number of preparations; estimates were at 25° C. The p' values are calculated from the Perrin equation on the assumption that the rotations are not hindered (see text footnote 1 [Cogan and Schachter.(1981)])

In contrast to the consistent differences in fluorescence anisotropy (Table 4), the $\tau$ values for each probe listed in Table 5 do not differ significantly with the route of loading. Accordingly, it is reasonable to suggest that the observed anisotropy differences signify greater motional freedom of the probe molecules in the outer as compared to the inner membrane leaflet. Inasmuch as our results do not further resolve motional freedom into the components of rate of rotation vs. extent of rotation, a true rotational relaxation time cannot be calculated from the Perrin relationship. Table 4 does include, however, values of an apparent rotational relaxation time, $\rho'$, calculated on the assumption of unhindered rotations. The ratios of $\rho'$ in ghost-loaded as compared to RBC-loaded membranes fall in a relatively narrow range, 1.7–2.0, for all probes tested, whereas the absolute values of $\rho'$ vary over 10-fold for the different compounds.

Excimer Fluorescence

Figure 7:
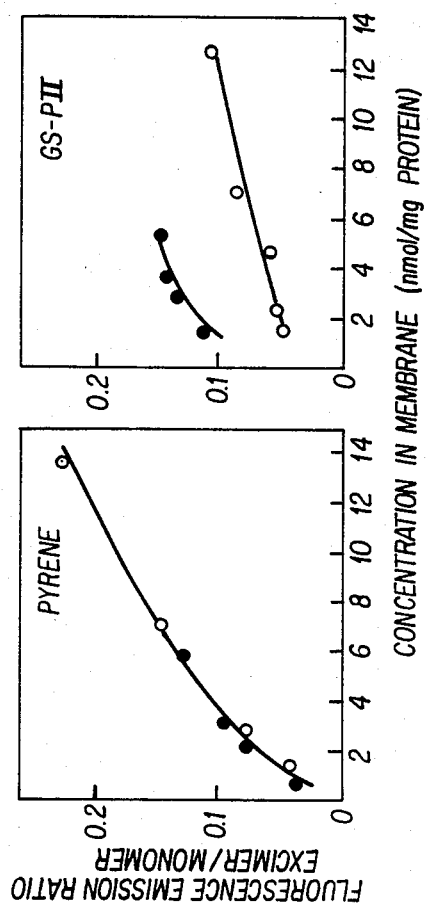
FIG. 7 is a graphical representation of excimer/monomer fluorescence ratio as a function of pyrene or glutathione-pyrene II concentration in membranes.
Figure 8:
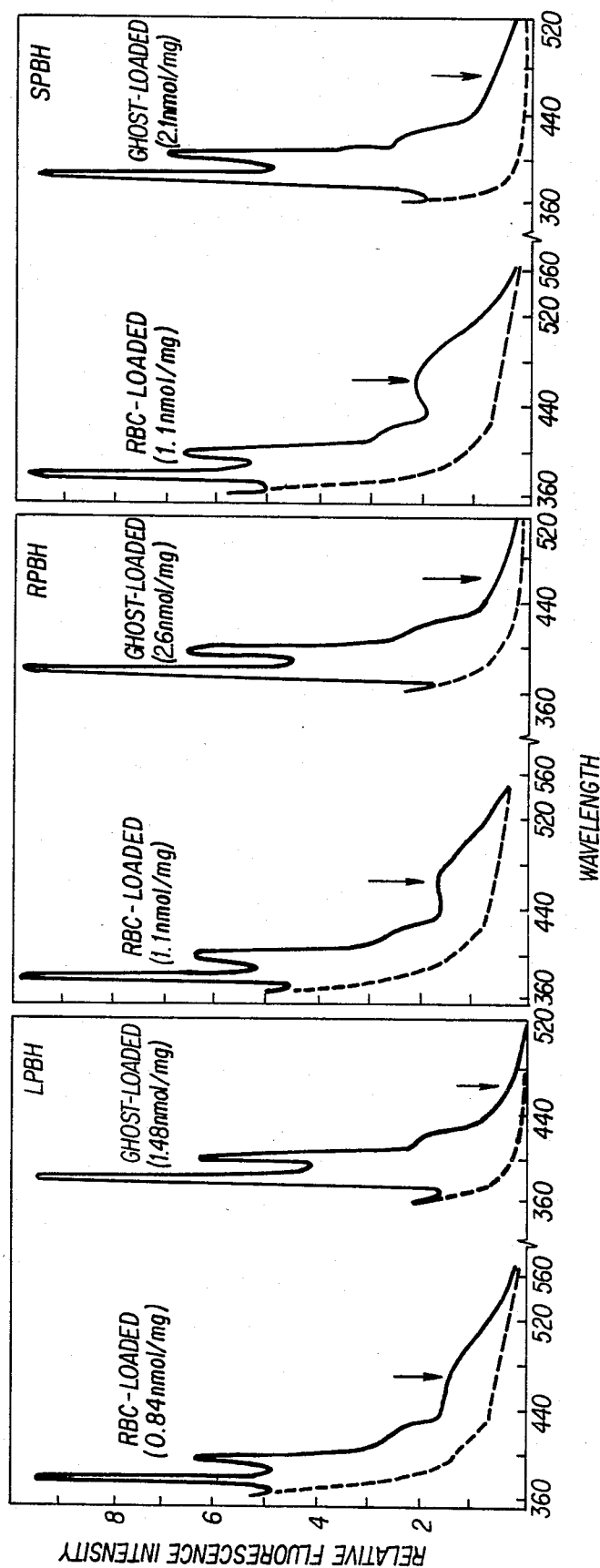
FIG. 8 is a representation of emission spectra of LPBH, RPBH and SPBH in erythrocyte-loaded and ghostloaded membranes.

Formation of the pyrene excimer is diffusion controlled and dependent on the fluidity of the microenvironment. Several investigators have utilized the excimer fluorescence to assess the fluidity of bilayer membranes. Accordingly, it was of interest to compare the excimer fluorescence of erythrocyte-loaded and ghost- loaded membrane preparations. FIG. 7 shows the results of studies with GS-PII and pyrene in which the excimer-/monomer fluorescence intensity ratio is plotted against probe concentration in the membrane. As expected, excimer fluorescence increases with the concentration of each compound. Pyrene, a permeant compound, however, yields excimer/monomer ratios which are independent of the route of loading, whereas the ratios for the impermeant GS-PII are considerably greater in the erythrocyte-loaded (outer leaflet) as compared to the ghost-loaded preperations. The oligosaccharide derivatives, LPBH, RPBH, and SPBH, also show greater excimer fluorescence in erythrocyte-loaded membranes, as illustrated in FIG. 8. In contrast to the other impermeant fluorophores, GS-PI yielded little or no excimer fluorescence under the test conditions.

Liposome Studies

Sonicated dispersions of erythrocyte membrane lipid were loaded with impermeant fluorophores as described supra. The resulting fluorescence studies are summarized in Table 6.

TABLE 6

Fluorescence Anisotropy of Impermeant Pyrene Fluorophores in Sonicated Dispersions of Erythrocyte Membrane Lipid

| probe | no. of preparations | fluorescence anisotrophy[a] r | $[(r_o/r)-1]^{-1}$ |
|---|---|---|---|
| RPBH  | 2 | 0.018 | 0.18 |
| SPBH  | 2 | 0.017 | 0.17 |
| GS-PI | 1 | 0.079 | 0.78 |
| GS-PII | 2 | 0.053 | 0.36 |

[a]Mean values are shown for the indicated number of preparations. Anisotropy estimations were at 25° C.

Values of the fluorescence anisotropy and $[(r_o/r)-1]^{-1}$ for RPBH, SPBH and GS-PII fall between the corresponding values for the erythrocyte-loaded and ghost-loaded membrane preparations (Tables 3 and 4) whereas the GS-PI values are somewhat less than those observed in the membranes. Again, the values for GS-PI exceed those of GS-PII.

Extraction of Extrinsic Proteins

For determination of whether the asymmetry of fluorescence anisotropy in the outer and inner leaflets is due to the influence of spectrin and erythrocyte actin, major extrinsic proteins of the endofacial surface were extracted. Ghost membranes were loaded with GS-PII, RPBH, or SPBH as previously described, and the membranes were extracted with 0.1 mM $Na_2EDTA$, pH 8, to remove most of the Coomassie brilliant blue stained bands 1, 2, and 5 as described supra. Removal of the protein had no significant effect on the fluorescence anisotropy of any of these probes.

The techniques and results presented hereinabove clearly demonstrate the application and potential of the impermeant fluorophores in the study of lipid dynamics of the individual hemileaflets and their significance in the elucidation of membrane function.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. An impermeant spectroscopic probe, comprising: glutathione joined by a linkage group to a spectroscopic reporter group, wherein
   (1) said linkage group is selected from the group consisting of

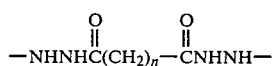

wherein n is 2, 4, 6, 8 or 10;

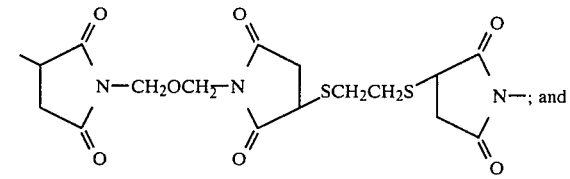

(2) said spectroscopic reporter group is selected from the group consisting of pyrenes, nitrobenz-oxa-diazoles, anthracenes, coumarins, acridines, anthranilates, bimanes, stilbenes, parinaric acids, and N-oxyl-4,4-dimethyloxayolidine derivatives of ketostearic acids or 2,2,5,5-tetramethyl-3-pyrrolin-1-oxyl-3-carboxylic acid.

2. The spectroscopic probe of claim 1 wherein said linkage group is

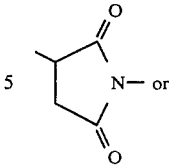

and said reporter is a pyrene.

3. The spectroscopic probe according to claim 1, wherein said probe is 2-(S-glutathionyl)-N-(1-pyrenyl)-succinimide.

4. The spectroscopic probe according to claim 1 wherein said pyrene is pyrenebutyryl hydrazide, N-(1-pyrenyl) maleimide, N-(1-pyrenyl) iodoacetamide, pyrenebutyric acid, pyrene decanoic acid, pyrenehexadecanoic acid or pyrene isothiocyanate.

5. The spectroscopic probe according to claim 1 wherein said nitrobenz-oxa-diazole is 7-nitrobenz-2-oxa-1,3-diazole, N-(NBD-4-yl) aziridine, 6-(NBD-4-yl) aminohexanoic acid or 12-(N-methyl-N-NBD-4-yl) aminododecanoic acid.

6. The spectroscopic probe according to claim 1 wherein said anthracene is 12-(9-anthroyloxy)stearic acid or 7-(9-anthroyloxy)stearic acid.

* * * * *